US012661349B1

(12) United States Patent
Chun et al.

(10) Patent No.: US 12,661,349 B1
(45) Date of Patent: Jun. 23, 2026

(54) PHARMACEUTICALLY ACCEPTABLE SALT OF SPHINGOSINE-1-PHOSPHATE RECEPTOR AGONIST, AND CRYSTALLINE FORM THEREOF

(71) Applicant: LG CHEM, LTD., Seoul (KR)

(72) Inventors: Seul Ah Chun, Seoul (KR); Sung Wook Kim, Seoul (KR); Ji Yoon Kim, Seoul (KR); Sung Won Kim, Seoul (KR); Ki Sook Park, Cheongju-si (KR)

(73) Assignee: LG CHEM, LTD., Seoul (KR)

( * ) Notice: Subject to any disclaimer, the term of this patent is extended or adjusted under 35 U.S.C. 154(b) by 441 days.

(21) Appl. No.: 18/555,209

(22) PCT Filed: Apr. 13, 2022

(86) PCT No.: PCT/KR2022/005378
§ 371 (c)(1),
(2) Date: Oct. 12, 2023

(87) PCT Pub. No.: WO2022/220601
PCT Pub. Date: Oct. 20, 2022

(30) Foreign Application Priority Data

Apr. 14, 2021 (KR) ........................ 10-2021-0048829

(51) Int. Cl.
*C07D 401/12* (2006.01)
*A61K 31/454* (2006.01)

(52) U.S. Cl.
CPC .......... *A61K 31/454* (2013.01); *C07D 401/12* (2013.01)

(58) Field of Classification Search
CPC ............................ A61K 31/454; C07D 401/12
See application file for complete search history.

(56) References Cited

U.S. PATENT DOCUMENTS

| | | | |
|---|---|---|---|
| 10,166,250 B2 | 1/2019 | Thomas et al. | |
| 2008/0200535 A1 | 8/2008 | Ohmori | |
| 2015/0376173 A1 | 12/2015 | Paek et al. | |
| 2023/0330077 A1 | 10/2023 | Kim et al. | |

FOREIGN PATENT DOCUMENTS

| | | |
|---|---|---|
| EP | 1826197 A1 | 8/2007 |
| EP | 4212159 A1 | 7/2023 |
| JP | 2009-137969 A | 6/2009 |
| JP | 2009-269819 A | 11/2009 |
| JP | 2010-510250 A | 4/2010 |
| JP | 2013-501074 A | 1/2013 |

(Continued)

OTHER PUBLICATIONS

Berge et al., "Review Article: Pharmaceutical Salts", Journal of Pharmaceutical Sciences, Jan. 1977, vol. 66, No. 1, pp. 1-19, XP 55515920.

(Continued)

*Primary Examiner* — Brandon J Fetterolf
(74) *Attorney, Agent, or Firm* — ROTHWELL, FIGG, ERNST & MANBECK, P.C.

(57) ABSTRACT

The present invention relates to a pharmaceutically acceptable salt of a sphingosine-1-phosphate receptor agonist and a crystalline form thereof, and more specifically, to a potassium salt or methanesulfonate of 1-[1-chloro-6-(3-chloro-1-isopropyl-1H-indazol-5-ylmethoxy)-3,4-dihydro-naphthalen-2-ylmethyl]-piperidine-4-carboxylic acid of formula 1, and a crystalline form thereof.

14 Claims, 2 Drawing Sheets

(56) References Cited

FOREIGN PATENT DOCUMENTS

| | | | | |
|---|---|---|---|---|
| JP | 2016-513126 | A | | 5/2016 |
| KR | 10-2014-0104376 | A | | 8/2014 |
| KR | 1020140104.76 | A | * | 8/2014 |
| WO | 2008-064320 | A2 | | 5/2008 |
| WO | 2014-129796 | A1 | | 8/2014 |
| WO | 2022-065939 | A1 | | 3/2022 |

OTHER PUBLICATIONS

Choi et al., "Polymorph control technology of active pharmaceutical substances", News & Information for Chemical Engineers, 2010, vol. 28, No. 1, pp. 38-46.
Extended European Search Report issued for European Patent Application No. 22788456.6. on Jul. 22, 2024, 7 pages.
Office Action issued for Korean Patent Application No. 10-2022-0045965 on Aug. 1, 2024, 6 pages.
Byrn, et al., "Pharmaceutical Solids: A Strategic Approach to Regulatory Considerations", Pharmaceutical Research, vol. 12, No. 7, 1995, pp. 945-954.
International Search Report issued in corresponding International Application No. PCT/KR2022/005378 dated Jul. 15, 2022, 8 pages.
Caira, Crystalline Polymorphism of Organic Compounds, Topics in Current Chemistry, 1998, No. 198, pp. 163-208.
Stahl et al., Handbook of Pharmaceutical Salts: Properties, Selection, and Use, VHCA; The Wiley-VCH, 2002, and pp. 329-350.
The Ministry of Health, Labour and Welfare, the Japanese Pharmacopoeia Seventeenth Edition: 2.58 X-Ray Powder Diffraction Method, 2016, pp. 71-74.
Bastin et al., Salt Selection and Optimisation Procedures for Pharmaceutical New Chemical Entities, Organic Process research & Development, 2000, vol. 4, pp. 427-435, DOI:10.1021/op000018u.
Kojima, Aiming to improve the efficiency of crystal form selection in drugs development, Pharmacology, 2008, vol. 68, No. 5, and pp. 344-349.
Toyokura et al., The Science of Pharmaceutical Polymorphism and Crystallization—Development, manufacturing and regulation trends: Chapter 9: Salt and crystalline form; studies , drug substance and formulation research, Maruzen Planet Co., Ltd., Sep. 20, 2002, pp. 305-317.
Office Action of the corresponding Japanese Patent Application No. 2023-563073 on Nov. 11, 2024, 10 pages.

* cited by examiner

[Figure 1]
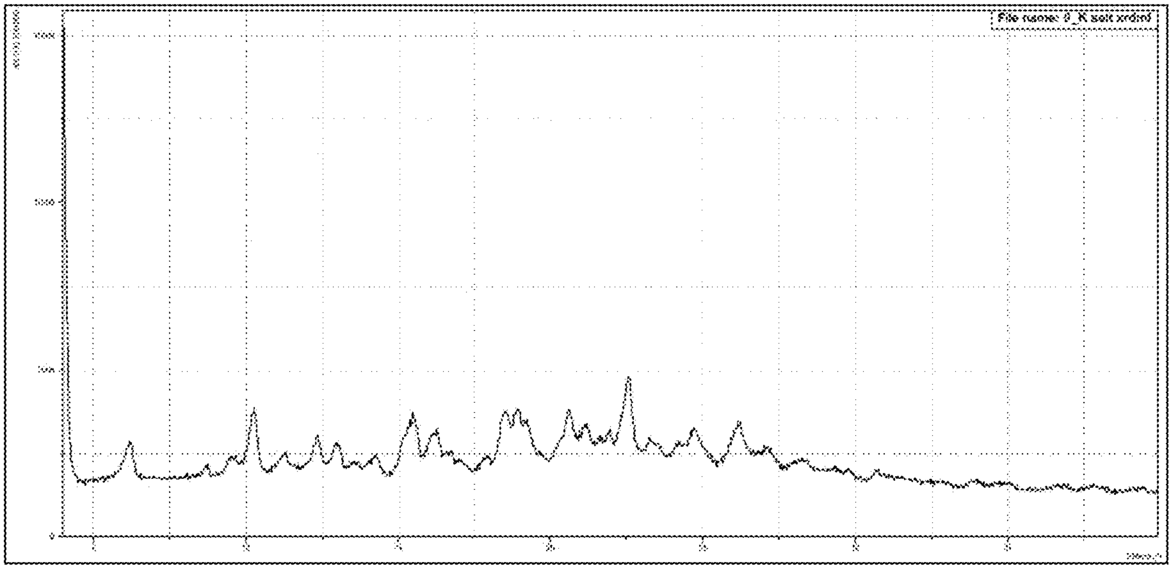
[Figure 2]
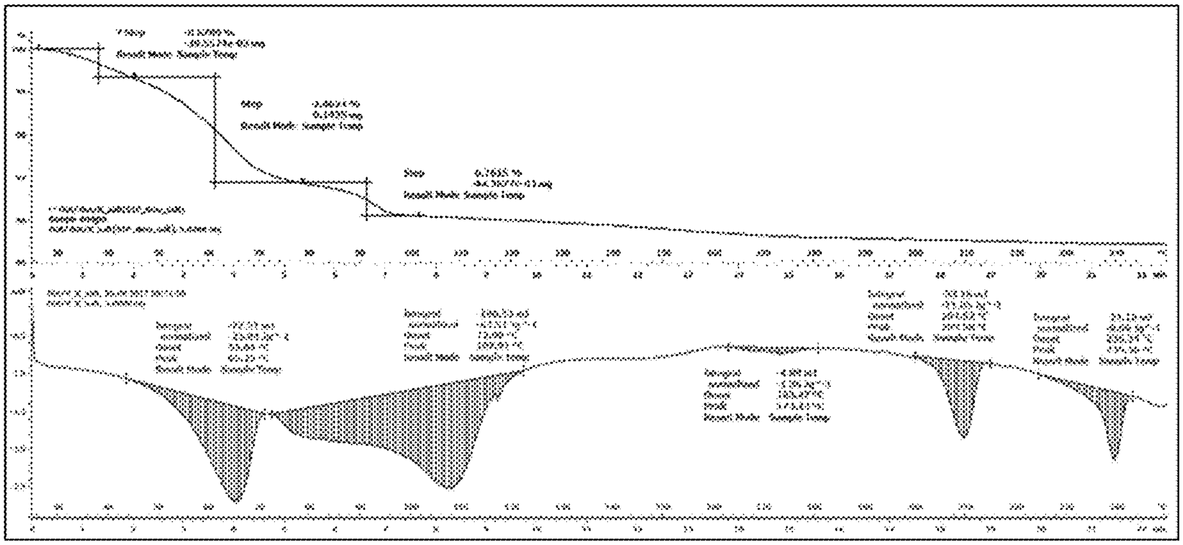

[Figure 3]
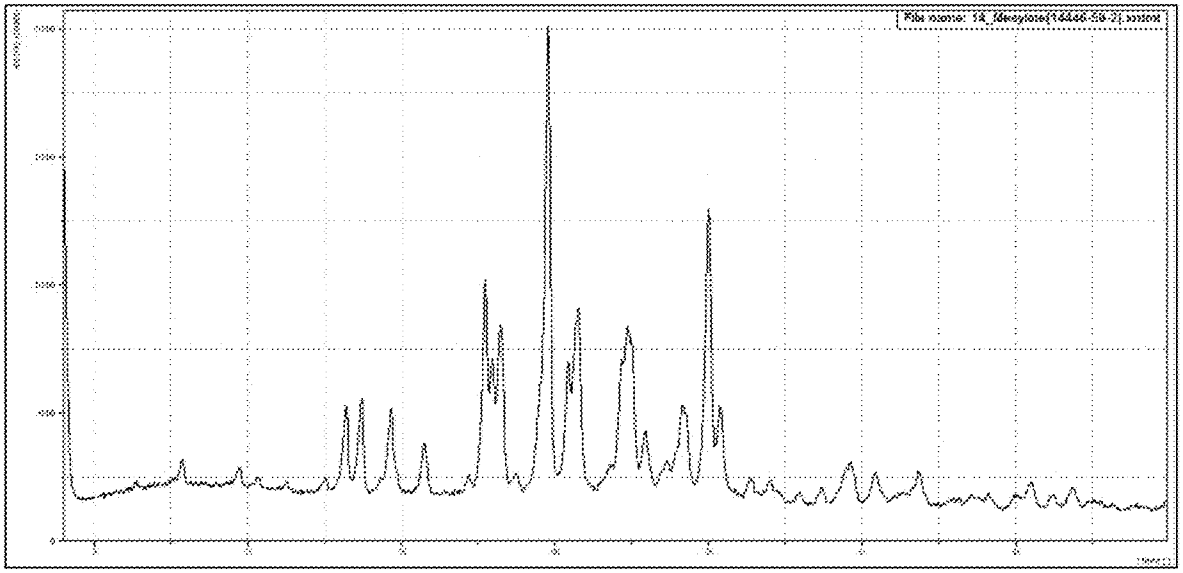
[Figure 4]
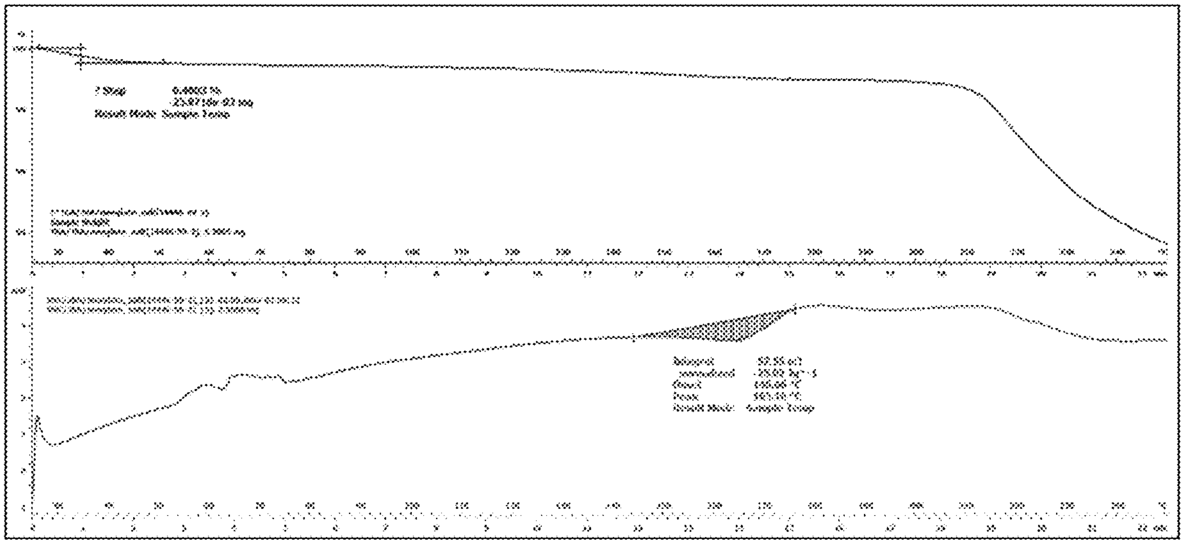

PHARMACEUTICALLY ACCEPTABLE SALT OF SPHINGOSINE-1-PHOSPHATE RECEPTOR AGONIST, AND CRYSTALLINE FORM THEREOF

CROSS REFERENCE TO RELATED APPLICATIONS

This application is a 35 U.S.C. § 371 National Phase Entry Application from PCT/KR2022/005378, filed on Apr. 13, 2022, designating the United States, and also claims priority to and the benefit of Korean Application No. 10-2021-0048829, filed on Apr. 14, 2021, the disclosures of which are incorporated herein by reference in their entirety.

TECHNICAL FIELD

The present invention relates to pharmaceutically acceptable salts of sphingosine-1-phosphate receptor agonist and crystalline forms thereof. More specifically, the present invention relates to potassium salt or methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid of the following Formula 1, and crystalline forms thereof:

[Formula 1]

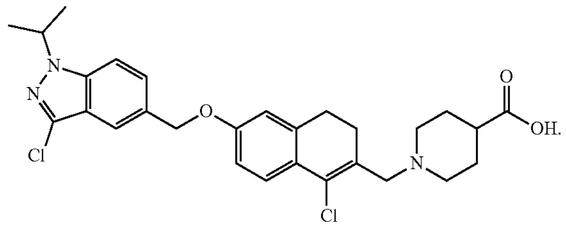

BACKGROUND ART

Sphingosine-1-phosphate (S1P) is produced via an intracellular ceramide pathway, in which ceramide is the starting material. Ceramide is produced via two pathways, the first of which is a de novo biosynthetic pathway. Ceramide is also produced by the degradation of sphingomyelin, a cell membrane constituent, in a cell. The S1P level in each tissue is controlled by two biosynthetic sphingosine kinases (SphKs) and two biodegradable S1P phosphatases (S1P lyase and lysophospholipid phosphatases). S1P—which is produced via phosphorylation of sphingosine by sphingosine kinase—is known to mediate various cellular responses, such as cell proliferation, cytoskeletal organization and migration, adherence- and tight junction assembly, and morphogenesis. S1P exists as a combined form with plasma protein including albumin at high level (100-1,000 nM) in plasma, while it is at a low level in tissues.

S1P binds with S1P receptor, a G-protein coupled receptor, to show various biological functions. As S1P receptor sub-types, S1P1 to S1P5 are known up to now and are named endothelial differentiation gene (EDG) receptors 1, 5, 3, 6 and 8, respectively. The S1P receptors are known to be involved in various biological functions such as leukocyte recirculation, neural cell proliferation, morphological changes, migration, endothelial function, vasoregulation and cardiovascular development.

In recent years, many studies have found that the S1P signaling process via these receptors plays an important role in a series of responses related to multiple sclerosis including inflammation response and the repair process, and a non-selective S1P1 agonist was actually approved as a therapeutic agent for multiple sclerosis. S1P receptors are extensively expressed in many cells related to the induction of multiple sclerosis. Specifically, S1P1 receptor plays a major role in the immune system. S1P1 receptor is mainly expressed on the surface of lymphocytes such as T cell and B cell, and responds to S1P resulting in involvement in recirculation of lymphocytes. In normal condition, the S1P concentration is higher in body fluid than in lymphoid tissue, and therefore lymphocytes leave lymphoid tissue by the difference of S1P concentration to circulate after efferent lymph circulates. However, if S1P1 receptor in lymphocytes is down-regulated by S1P1 agonist, the egress of lymphocytes from lymphoid tissue does not occur, resulting in reduced infiltration of autoaggressive lymphocytes which cause inflammation and tissue damage in the central nervous system (CNS). As a result, a therapeutic effect on multiple sclerosis is obtained. Fingolimod, a non-selective S1P1 agonist, has been approved as an oral medication for the treatment of multiple sclerosis. When it binds at S1P1 receptor to be activated, the receptor becomes degraded or internalized from the surface of lymphocytes ironically, and thus it acts as a functional S1P1 antagonism.

In relation to the S1P receptor, International Publication No. WO 2014/129796 (publication date: Aug. 28, 2014) discloses compounds effective as an S1P receptor agonist. Although the activity of the compounds as an S1P receptor agonist is excellent, there is a need for development of a form having improved solubility to improve bioavailability and better pharmaceutical properties such as thermal stability and moisture stability.

DISCLOSURE OF INVENTION

Technical Problem

The present invention is intended to provide pharmaceutically acceptable salts of 1-[1-chloro-6-(3-chloro-1-isopropyl-1H-indazol-5-ylmethoxy)-3,4-dihydro-naphthalen-2-ylmethyl]-piperidine-4-carboxylic acid of the following Formula 1 and crystalline forms thereof having excellent pharmaceutical properties:

[Formula 1]

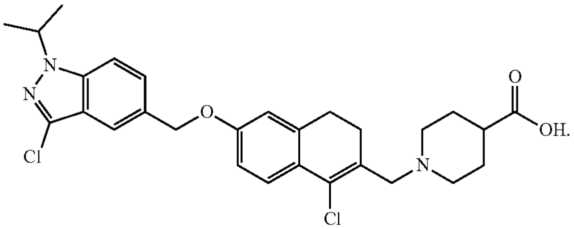

Solution to Problem

In order to solve the above technical problem, the present invention provides a potassium salt of 1-[1-chloro-6-(3-chloro-1-isopropyl-1H-indazol-5-ylmethoxy)-3,4-dihydronaphthalen-2-ylmethyl]-piperidine-4-carboxylic acid and a crystalline form thereof.

In addition, the present invention provides a methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid and a crystalline form thereof.

Furthermore, the present invention provides a pharmaceutical composition comprising the potassium salt or methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid or a crystalline form thereof as an active ingredient, together with a pharmaceutically acceptable carrier.

The present invention is described in detail hereinafter.

According to one aspect of the present invention, there is provided a potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid.

In one embodiment according to the present invention, the potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid may be in a crystalline form.

In one embodiment according to the present invention, the crystalline form of potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid has 3 or more, 5 or more, 7 or more, 9 or more, or 10 or more characteristic peaks (2θ) selected from the following X-ray diffraction pattern spectrum: 6.14±0.2°, 9.59±0.2°, 10.23±0.2°, 11.25±0.2°, 12.32±0.2°, 12.98±0.2°, 15.39±0.2°, 16.18±0.2°, 18.47±0.2°, 18.89±0.2°, 19.22±0.2°, 20.57±0.2°, 21.14±0.2°, 21.91±0.2°, 22.50±0.2°, 23.34±0.2°, 24.16±0.2°, 24.70±0.2°, 26.12±0.2° and 27.03±0.2°.

In one embodiment according to the present invention, the crystalline form of potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid has 3 or more, 5 or more, 7 or more, 9 or more, or 10 or more characteristic peaks (2θ) selected from the following X-ray diffraction pattern spectrum: 6.14±0.1°, 9.59±0.1°, 10.23±0.1°, 11.25±0.1°, 12.32±0.1°, 12.98±0.1°, 15.39±0.1°, 16.18±0.1°, 18.47±0.1°, 18.89±0.1°, 19.22±0.1°, 20.57±0.1°, 21.14±0.1°, 21.91±0.1°, 22.50±0.1°, 23.34±0.1°, 24.16±0.1°, 24.70±0.1°, 26.12±0.1° and 27.03±0.1°.

When the crystalline form of potassium salt is subjected to thermogravimetric analysis (TGA), a weight loss of about 3.9% is observed at about 30-100° C. When the crystal form of potassium salt is analyzed by using differential scanning calorimetry (DSC), a broad endothermic peak is observed at a position of about 45-125° C. corresponding to the initial weight loss of TGA, and when further heated, endotherms are observed at about 173° C., 205° C. and 236° C. (onset). When the crystalline form of potassium salt is quantitatively analyzed by HPLC (high performance liquid chromatography), water solubility is 33238.5 μg/mL.

According to another aspect of the present invention, there is provided a methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid.

In one embodiment according to the present invention, the methanesulfonic acid salt of 1-[1-chloro-6-(3-chloro-1-isopropyl-1H-indazol-5-ylmethoxy)-3,4-dihydro-naphthalen-2-ylmethyl]-piperidine-4-carboxylic acid may be in a crystalline form.

In one embodiment according to the present invention, the crystalline form of methanesulfonic acid salt of 1-[1-chloro-6-(3-chloro-1-isopropyl-1H-indazol-5-ylmethoxy)-3,4-dihydro-naphthalen-2-ylmethyl]-piperidine-4-carboxylic acid has 3 or more, 5 or more, 7 or more, 9 or more, or 10 or more characteristic peaks (2θ) selected from the following X-ray diffraction pattern spectrum: 13.16±0.2°, 13.65±0.2°, 14.62±0.2°, 15.71±0.2°, 17.95±0.2°, 18.21±0.2°, 19.73±0.2°, 20.70±0.2°, 22.31±0.2°, 22.49±0.2°, 22.92±0.2°, 24.23±0.2°, 24.95±0.2°, 25.35±0.2°, 29.52±0.2° and 31.78±0.2°.

In one embodiment according to the present invention, the crystalline form of methanesulfonic acid salt of 1-[1-chloro-6-(3-chloro-1-isopropyl-1H-indazol-5-ylmethoxy)-3,4-dihydro-naphthalen-2-ylmethyl]-piperidine-4-carboxylic acid has 3 or more, 5 or more, 7 or more, 9 or more, or 10 or more characteristic peaks (2θ) selected from the following X-ray diffraction pattern spectrum: 13.16±0.1°, 13.65±0.1°, 14.62±0.1°, 15.71±0.1°, 17.95±0.1°, 18.21±0.1°, 19.73±0.1°, 20.70±0.1°, 22.31±0.1°, 22.49±0.1°, 22.92±0.1°, 24.23±0.1°, 24.95±0.1°, 25.35±0.1°, 29.52±0.1° and 31.78±0.1°.

When the crystalline form of methanesulfonic acid salt is subjected to thermogravimetric analysis (TGA), a weight loss of about 0.5% is observed at an initial temperature of less than about 50° C. When the crystalline form of methanesulfonic acid salt is analyzed by using differential scanning calorimetry (DSC), an endothermic peak is observed at about 148° C. When the crystalline form of methanesulfonic acid salt is quantitatively analyzed by HPLC (high performance liquid chromatography), water solubility is 536.8 μg/mL.

According to still another aspect of the present invention, there is provided a pharmaceutical composition comprising the potassium salt or methanesulfonic acid salt of 1-[1-chloro-6-(3-chloro-1-isopropyl-1H-indazol-5-ylmethoxy)-3,4-dihydro-naphthalen-2-ylmethyl]-piperidine-4-carboxylic acid, together with a pharmaceutically acceptable carrier.

In the present invention, a "pharmaceutical composition" may include other components such as carriers, diluents, excipients, etc., in addition to the active ingredient of the present invention. Accordingly, the pharmaceutical composition may include pharmaceutically acceptable carriers, diluents, excipients or combinations thereof, if necessary. The pharmaceutical composition facilitates the administration of compounds into the body. Various methods for administering the compounds include, but are not limited to, oral, injection, aerosol, parenteral and local administration.

Herein, a "carrier" means a compound that facilitates the addition of compounds into the cell or tissue. For example, dimethylsulfoxide (DMSO) is a conventional carrier facilitating the administration of many organic compounds into living cells or tissues.

Herein, a "diluent" means a compound that not only stabilizes a biologically active form but is diluted in solvent dissolving the compounds. A dissolved salt in buffer is used as a diluent in this field. A conventionally used buffer is a phosphate buffer saline mimicking salt form in body fluid. Since a buffer solution can control the pH of the solution at low concentration, a buffer diluent hardly modifies the biological activity of compounds.

Herein, "pharmaceutically acceptable" means such property that does not impair the biological activity and physical property of compounds.

In the present invention, the potassium salt or methanesulfonic acid salt of the compound of Formula 1 can be formulated as various pharmaceutically administered dosage forms. In the preparation of the pharmaceutical composition of the present invention, an active component—specifically, the potassium salt or methanesulfonic acid salt of the compound of Formula 1 or a pharmaceutically acceptable salt thereof—is mixed with selected pharmaceutically acceptable carriers considering the dosage form to be prepared. For example, the pharmaceutical composition of the present invention can be formulated as injections, oral preparations and the like, as needed.

The potassium salt or methanesulfonic acid salt of the compound of Formula 1 of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or stabilizing agents. In addition, the compound may be, for example, dry powder form which is dissolved in sterilized pyrogen-free water before use. The potassium salt or methanesulfonic acid salt of the compound of Formula 1 of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the crystalline form of the compound of Formula 1 of the present invention with at least one carrier selected from inert diluents such as sucrose, lactose or starch, lubricants such as magnesium stearate, disintegrating agents, binders and the like. In addition, it may be formulated as a transdermal dosage form—for example, as a lotion, ointment, gel, cream, patch or spray.

The pharmaceutical composition according to the present invention is suitable for preventing or treating diseases related to sphingosine-1-phosphate receptor. In one embodiment according to the present invention, the pharmaceutical composition may be used in the treatment of autoimmune disease including multiple sclerosis. In one embodiment according to the present invention, the pharmaceutical composition may be used in the prevention or treatment of a disease caused by undesired lymphocyte infiltration related to sphingosine-1-phosphate. In one embodiment according to the present invention, the pharmaceutical composition may be used in the prevention or treatment of immunoregulation disorder. In one embodiment according to the present invention, examples of the immunoregulation disorder may be autoimmune disease or chronic inflammatory disease selected from the group consisting of systemic lupus erythematosus, chronic rheumatoid arthritis, inflammatory bowel diseases, multiple sclerosis, amyotrophic lateral sclerosis (ALS), arteriosclerosis, atherosclerosis, scleroderma and autoimmune hepatitis, but are not limited thereto.

Herein, the term "prevention" refers to reducing or eliminating the possibility of contracting a disease.

Herein, the term "treatment" is used to mean deterring, delaying or ameliorating the progress of diseases in a subject exhibiting symptoms of diseases.

Effects of the Invention

The potassium salt or methanesulfonic acid salt of 1-[1-chloro-6-(3-chloro-1-isopropyl-1H-indazol-5-ylmethoxy)-3,4-dihydro-naphthalen-2-ylmethyl]-piperidine-4-carboxylic acid, and crystalline forms thereof according to the present invention have pharmacological activity as a sphingosine-1-phosphate receptor agonist and at the same time have excellent bioavailability due to high solubility as well as excellent pharmaceutical properties such as stability—for example, thermal stability and storage stability.

BRIEF DESCRIPTION OF DRAWINGS

FIG. 1 is an X-ray powder diffraction (XRPD) spectrum of the crystalline form of potassium salt.

FIG. 2 is thermogravimetric analysis (TGA)/differential scanning calorimetry (DSC) analysis results of the crystalline form of potassium salt.

FIG. 3 is an X-ray powder diffraction (XRPD) spectrum of the crystalline form of methanesulfonic acid salt.

FIG. 4 is thermogravimetric analysis (TGA)/differential scanning calorimetry (DSC) analysis results of the crystalline form of methanesulfonic acid salt.

MODE FOR THE INVENTION

Hereinafter, the present invention is explained in more detail with the following examples. However, it must be understood that the protection scope of the present invention is not limited to the examples.

Preparation Example: Synthesis of 1-[1-chloro-6-(3-chloro-1-isopropyl-1H-indazol-5-ylmethoxy)-3,4-dihydro-naphthalen-2-ylmethyl]-piperidine-4-carboxylic acid 1-[1-Chloro-6-(3-chloro-1-isopropyl-1H-indazol-5-ylmethoxy)-3,4-dihydro-naphthalen-2-ylmethyl]-piperidine-4-carboxylic acid (hereinafter referred to as "Compound 1") was prepared according to the method described in Example 153 of International Publication No. WO 2014/129796 A1.

Example 1: Preparation of Potassium Salt and Crystalline Form 3 g of Compound 1 (free form), 30 mL of methanol, 1 equivalent of potassium hydroxide and 1 mL of water were added to a reactor and stirred. The solution was heated (60° C.), but the suspension was maintained, and so the solvent was removed by cooling (room temperature) and distillation under reduced pressure. After dissolving the solid by adding 6 mL of dichloromethane, the crystallization was carried out with 30 mL of methyl tert-butyl ether as an anti-solvent.

Example 2: Analysis of Crystalline Form of Potassium Salt (1) XRPD (x-Ray Powder Diffraction) XRPD analysis was carried out by using a PANalytical X'pert Pro MPD diffractometer with an incident beam of Cu radiation. After compacting about 20-30 mg of the sample to have a flat surface on the glass sample holder, the generator of the equipment was set to 45 kV (acceleration voltage) and 40 mA (filament emission), and then the measurement was conducted with reflection mode (not-spin). Bragg angles (20) in the range of 4 to 400 were measured with 0.026° of step size and 51 seconds of time per step conditions. XRPD patterns were classified and processed using HighScore Plus 2.2c software, and the results are represented in FIG. 1 and Table 2.

(2) DSC (Differential Scanning Calorimetry)

DSC was carried out by using a Mettler Toledo DSC 1 system. About 2-5 mg of sample was weighed and placed in a 40 μL Al crucible (flat-bottomed aluminum pan with one pin-hole lid), and one pin-hole was made. Then, the sample was heated from 25° C. to 350° C. at a rate of 10° C./min to measure DSC. During the measurement, nitrogen gas was supplied to the inside of the instrument at a rate of 70 mL/min to prevent the inflow of oxygen and other gases. Data collection and evaluation was performed by using the software STARe (FIG. 2).

(3) TGA (Thermogravimetric Analysis)

TGA was carried out by using a Mettler Toledo TGA/DSC 1 module. About 4-8 mg of sample was weighed and placed in a 100 μL Al crucible (flat-bottomed aluminum crucible). Then, the sample was heated from 30° C. to 350° C. at a rate of 10° C./min to measure TGA. During the measurement, nitrogen gas was supplied to the inside of the instrument at a rate of 80 mL/min to prevent the inflow of oxygen and other gases. Data collection and evaluation was performed by using the software STARe (FIG. 2).

(4) Quantitative Analysis (HPLC)

Approximately 26.7 mg of the sample was precisely weighed and placed in a 500 mL volumetric flask. 450 mL of a diluted solution (methanol:purified water=1:1) was added thereto, completely dissolved, and then filled with the diluted solution up to the marked line. HPLC equipment and analysis methods are represented in Table 1 below.

TABLE 1

| | |
|---|---|
| Column | YMC-Triart C18 3 μm, 4.6 × 250 mm, YMC |
| Injection volume | 10 μL |
| Flow rate | 0.5 mL/min |
| Column temperature | 10° C. |
| Detection wavelength | 291 nm |
| Mobile phase A | 60:5:35:0.1 Acetonitrile/Methanol/$H_2O$/TFA |
| Mobile phase B | 85:5:10:0.1 Acetonitrile/Methanol/$H_2O$/TFA |
| Total running time | 45 minutes |

Gradient system

| Time (Min) | Mobile phase A (%) | Mobile phase B (%) |
|---|---|---|
| 0 | 100 | 0 |
| 5 | 85 | 15 |
| 18 | 85 | 15 |
| 23 | 0 | 100 |
| 26 | 0 | 100 |
| 27 | 100 | 0 |
| 45 | 100 | 0 |

(5) Results

As a result of XRPD analysis, it was confirmed that the compound was in a crystalline form.

TABLE 2

| No. | 2θ |
|---|---|
| 1 | 6.14 |
| 2 | 8.69 |
| 3 | 9.59 |
| 4 | 10.23 |
| 5 | 11.25 |
| 6 | 12.32 |
| 7 | 12.98 |
| 8 | 13.57 |
| 9 | 14.18 |
| 10 | 15.39 |
| 11 | 16.18 |
| 12 | 16.67 |
| 13 | 17.01 |
| 14 | 17.86 |
| 15 | 18.47 |
| 16 | 18.89 |

TABLE 2-continued

| No. | 2θ |
|---|---|
| 17 | 19.22 |
| 18 | 20.57 |
| 19 | 21.14 |
| 20 | 21.60 |
| 21 | 21.91 |
| 22 | 22.50 |
| 23 | 23.34 |
| 24 | 24.16 |
| 25 | 24.70 |
| 26 | 26.12 |
| 27 | 27.03 |
| 28 | 28.25 |
| 29 | 30.69 |
| 30 | 33.94 |

As a result of TGA measurement, a weight loss of about 3.9% was observed at about 30-100° C.

As a result of DSC measurement, a broad endothermic peak was observed at about 45-125° C. corresponding to the initial weight loss of TGA. When further heated, endotherms were observed at about 173° C., 205° C. and 236° C. (onset), which are expected to be endothermic peaks due to melting of the solid.

As a result of quantitative analysis by HPLC, the water solubility of the crystalline form of potassium salt was 33238.5 μg/mL.

Example 3: Preparation of Methanesulfonic Acid Salt and Crystalline Form

Methanesulfonic acid salt and crystalline form thereof were prepared by the following two methods.

(1) A solution in which 3 g of Compound 1 (free form), 30 mL of water and methanesulfonic acid are mixed was prepared. After cooling the solution with ice, 45 mL of methyl tert-butyl ether was added thereto. Then, washing was carried out with 9 mL of water.

(2) A solution in which 5 g of Compound 1 (free form), 25 mL of water and methanesulfonic acid are mixed was prepared. After cooling the solution with ice, 45 mL of methyl tert-butyl ether was added. Then, washing was carried out with a mixture of 15 mL of water/methyl tert-butyl ether.

Example 4: Analysis of Crystalline Form of Methanesulfonic Acid Salt (1) XRPD (x-Ray Powder Diffraction)

XRPD analysis was carried out in the same manner as in Example 2 (FIG. 3).

TABLE 3

| No. | 2θ |
|---|---|
| 1 | 7.80 |
| 2 | 9.67 |
| 3 | 10.32 |
| 4 | 11.20 |
| 5 | 12.47 |
| 6 | 13.16 |
| 7 | 13.65 |
| 8 | 14.62 |
| 9 | 15.71 |
| 10 | 17.15 |
| 11 | 17.71 |
| 12 | 17.95 |
| 13 | 18.21 |

TABLE 3-continued

| No. | 2θ |
|---|---|
| 14 | 18.70 |
| 15 | 19.73 |
| 16 | 20.40 |
| 17 | 20.70 |
| 18 | 22.10 |
| 19 | 22.31 |
| 20 | 22.49 |
| 21 | 22.92 |
| 22 | 23.62 |
| 23 | 24.07 |
| 24 | 24.23 |
| 25 | 24.95 |

TABLE 3-continued

| No. | 2θ |
|---|---|
| 26 | 25.35 |
| 27 | 26.34 |
| 28 | 26.97 |
| 29 | 27.91 |
| 30 | 28.65 |
| 31 | 29.52 |
| 32 | 30.40 |
| 33 | 31.78 |
| 34 | 33.57 |
| 35 | 34.08 |
| 36 | 34.98 |
| 37 | 35.44 |
| 38 | 36.16 |
| 39 | 36.80 |
| 40 | 37.65 |
| 41 | 39.80 |

(2) DSC (Differential Scanning Calorimetry) and TGA (Thermogravimetric Analysis)

DSC and TGA were carried out in the same manner as in Example 2 (FIG. 4).

(3) Quantitative Analysis (HPLC)

Quantitative analysis was carried out in the same manner as in Example 2.

(4) Results

As a result of XRPD analysis, it was confirmed that the compound was in a crystalline form.

As a result of TGA measurement, a weight loss of about 0.5% was observed at an initial temperature of less than about 50° C.

As a result of DSC measurement, an endothermic peak was observed at about 148° C., which is expected to be an endothermic peak due to melting of the solid.

As a result of quantitative analysis by HPLC, the water solubility of the crystalline form of methanesulfonic acid was 536.8 μg/mL.

Example 5: Comparison of Properties with Other Salt Forms

Various types of salts were prepared. After analyzing characteristics in the same manner as above, the comparisons with potassium salt and methanesulfonic acid salt (mesylate) are represented in Table 4 below.

TABLE 4

| Salts | Crystallinity (XRD) | Endothermic peak (° C., DSC, Onset) | Residual solvent (%, TGA) | Water solubility (μg/mL, HPLC) 24 hr |
|---|---|---|---|---|
| Free form | Crystalline | 202.4 | — | 3.7 |
| Maleate (1 eq.) | Amorphous | — | — | 15.4 |
| HBr salt (1 eq.) | Semi-crystalline | 120.4/165.9 (Exo; 138.5) | 3.7 | 11.8 |
| Phosphate (0.5 eq.) | Semi-crystalline | 104.9/130.0 | 5.3 | 15.5 |
| L-Tartarate (0.25 eq.) | Semi-crystalline | 99.6 | 4.2 | 12.0 |
| Citrate (1 eq.) | Semi-crystalline | 105.0/158.4 | 13.3 | 9.3 |
| Acetate (0.5 eq.) | Semi-crystalline | 92.2/199.1 | 2.6 | 4.7 |
| Succinate (0.5 eq.) | Semi-crystalline | 96.0/196.6 | 3.2 | 4.8 |
| Fumarate (4 eq.) | Semi-crystalline | 197.4 | — | 2.5 |
| K salt (1 eq.) | Semi-crystalline | 97.0/169.3/204.6/236.6 | 3.4 | 33238.5 |
| Ca salt (1 eq.) | Crystalline | 193.4 | 3.3 | 3.2 |
| Na salt (1 eq.) | Amorphous | — | — | 46309.6 |
| Mesylate (1 eq.) | Crystalline | 148.7/184.3 | 0.3 | 536.8 |
| Sulfate (0.5 eq.) | Semi-crystalline | 122.6 | 2.9 | 7.3 |

The invention claimed is:

1. A potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid, which has 3 or more characteristic peaks (2Θ) selected from the following X-ray diffraction pattern spectrum: 6.14±0.2°, 9.59±0.2°, 10.23±0.2°, 11.25±0.2°, 12.32±0.2°, 12.98±0.2°, 15.39±0.2°, 16.18±0.2°, 18.47±0.2° 18.89±0.2° 19.22±0.2°, 20.57±0.2°, 21.14±0.2°, 21.91±0.2°, 22.50±0.2°, 23.34±0.2°, 24.16±0.2° 24.70±0.2° 26.12±0.2° and 27.03±0.2°.

2. The potassium salt according to claim 1, which is in a crystalline form.

3. The potassium salt according to claim 1, which has 3 or more characteristic peaks (2Θ) selected from the following X-ray diffraction pattern spectrum: 6.14±0.1°, 9.59±0.1°, 10.23±0.1°, 11.25±0.1°, 12.32±0.1°, 12.98±0.1°, 15.39±0.1°, 16.18±0.1°, 18.47±0.1°, 18.89±0.1°, 19.22±0.1°, 20.57±0.1°, 21.14±0.1°, 21.91±0.1°, 22.50±0.1°, 23.34±0.1°, 24.16±0.1°, 24.70±0.1°, 26.12±0.1° and 27.03±0.1°.

4. A methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid, which has 3 or more characteristic peaks (2Θ) selected from the following X-ray diffraction pattern spectrum: 13.16±0.2°, 13.65±0.2°, 14.62±0.2°, 15.71±0.2°, 17.95±0.2°, 18.21±0.2° 19.73±0.2°, 20.70±0.2°, 22.31±0.2°, 22.49±0.2°, 22.92±0.2°, 24.23±0.2°, 24.95±0.2°, 25.35±0.2°, 29.52±0.2° and 31.78±0.2°.

5. The methanesulfonic acid salt according to claim 4, which is in a crystalline form.

6. The methanesulfonic acid salt according to claim 4, which has 3 or more characteristic peaks (2Θ) selected from the following X-ray diffraction pattern spectrum: 13.16±0.1°, 13.65±0.1°, 14.62±0.1°, 15.71±0.1°, 17.95±0.1°, 18.21±0.1°, 19.73±0.1°, 20.70±0.1°, 22.31±0.1°, 22.49±0.1°, 22.92±0.1°, 24.23±0.1°, 24.95±0.1°, 25.35±0.1°, 29.52±0.1° and 31.78±0.1°.

7. A pharmaceutical composition for the treatment of autoimmune disease including multiple sclerosis, which comprises a potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 1, together with a pharmaceutically acceptable carrier.

8. A pharmaceutical composition for the prevention or treatment of a disease caused by undesired lymphocyte infiltration related to sphingosine-1-phosphate, which comprises a potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 1, together with a pharmaceutically acceptable carrier.

9. A pharmaceutical composition for the prevention or treatment of immunoregulation disorder, which comprises a potassium salt of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 1, together with a pharmaceutically acceptable carrier.

10. The pharmaceutical composition according to claim 9, wherein the immunoregulation disorder is autoimmune disease or chronic inflammatory disease selected from the group consisting of systemic lupus erythematosus, chronic rheumatoid arthritis, inflammatory bowel diseases, multiple sclerosis, amyotrophic lateral sclerosis (ALS), arteriosclerosis, atherosclerosis, scleroderma and autoimmune hepatitis.

11. A pharmaceutical composition for the treatment of autoimmune disease including multiple sclerosis, which comprises a methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 4, together with a pharmaceutically acceptable carrier.

12. A pharmaceutical composition for the prevention or treatment of a disease caused by undesired lymphocyte infiltration related to sphingosine-1-phosphate, which comprises a methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 4, together with a pharmaceutically acceptable carrier.

13. A pharmaceutical composition for the prevention or treatment of immunoregulation disorder, which comprises a methanesulfonic acid salt (mesylate) of 1-[1-chloro-6-(3-chloro-1-isopropyl-1H-indazol-5-ylmethoxy)-3,4-dihydro-naphthalen-2-ylmethyl]-piperidine-4-carboxylic acid as defined in claim 4, together with a pharmaceutically acceptable carrier.

14. The pharmaceutical composition according to claim 13, wherein the immunoregulation disorder is autoimmune disease or chronic inflammatory disease selected from the group consisting of systemic lupus erythematosus, chronic rheumatoid arthritis, inflammatory bowel diseases, multiple sclerosis, amyotrophic lateral sclerosis (ALS), arteriosclerosis, atherosclerosis, scleroderma and autoimmune hepatitis.

* * * * *